United States Patent [19]

Monahan

[11] Patent Number: 5,349,397
[45] Date of Patent: Sep. 20, 1994

[54] APPARATUS AND METHOD FOR DETERMINING A PATIENT'S DOMINANT EYE

[76] Inventor: Patrick W. Monahan, 2744 Coral Ridge Rd., Rancho Palos Verdes, Calif. 90274

[21] Appl. No.: 84,306

[22] Filed: Jun. 29, 1993

[51] Int. Cl.$^5$ .............................. A61B 3/02; A61B 3/08
[52] U.S. Cl. .................................... 351/201; 351/222; 351/239; 351/244; 351/246
[58] Field of Search ............... 351/201, 200, 203, 239, 351/240, 244, 246, 222, 223, 245

[56] References Cited

U.S. PATENT DOCUMENTS

| | | | |
|---|---|---|---|
| 1,948,901 | 2/1934 | Brombach | 351/203 |
| 1,954,399 | 4/1934 | Ames | 351/201 |
| 2,033,634 | 3/1936 | Higley | 351/201 |
| 2,070,849 | 2/1937 | Sherman | 351/203 |
| 2,080,721 | 5/1937 | Kelly | 351/239 |
| 2,091,173 | 8/1937 | Wottring | 351/201 |
| 2,196,906 | 4/1940 | Sherman | 351/201 |
| 2,213,467 | 9/1940 | Greenspoon | 351/203 |
| 2,261,850 | 11/1941 | Kelly | 351/203 |
| 2,748,764 | 6/1956 | Boyd et al. | 351/203 |
| 2,837,086 | 6/1958 | Thorburn | 351/203 |
| 2,955,593 | 10/1960 | Sorenson | 351/203 |
| 4,778,267 | 10/1988 | Hillis et al. | 351/203 |

FOREIGN PATENT DOCUMENTS 0241387 10/1925 United Kingdom ............... 351/203

Primary Examiner—William L. Sikes
Assistant Examiner—David R. Parsons
Attorney, Agent, or Firm—Denton L. Anderson

[57] ABSTRACT

An examining device is provided which quickly and easily determines the "sidedness" of an individual's eyes. The device has a viewing port and conical opaque sidewalls which converge to a small diameter viewing port. The device is constructed so that the individual being tested can see with both eyes an object just beyond the end of the viewing port, but cannot see with both eyes an object which is relatively further away from the viewing port. A first blocking device is provided for alternatively blocking and unblocking the right eye line of sight of the person being examined. A second blocking device is provided for alternatively blocking and unblocking the left eye line of sight of the person being examined. The device is used by asking the individual being examined to look through the device to an object which is located relatively far beyond the end of the viewing port. While the device is held steady, the first blocking device is used to block the right eye line of sight. If the right eye of the individual being tested is the preferred eye, blocking the right eye line of sight with the first blocking device will cause the view of the object to be blocked. Alternatively, if the left eye of the individual being tested is preferred, blocking the right eye line of sight will not inhibit the view of the object. The device is light, small and quite portable. It is easily used in classroom or other group situations.

15 Claims, 3 Drawing Sheets

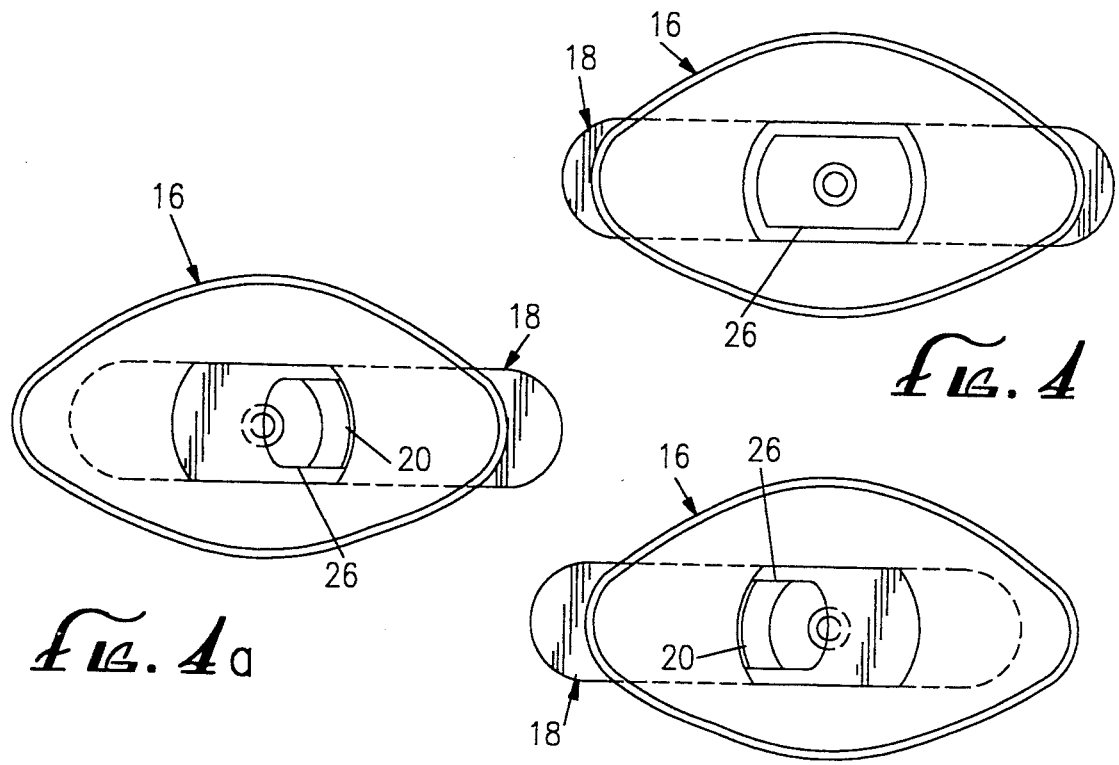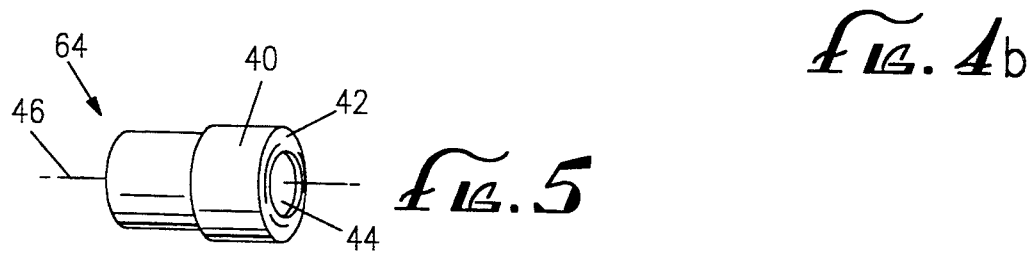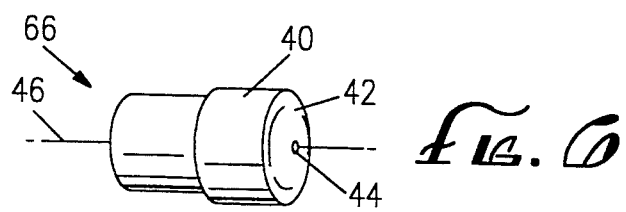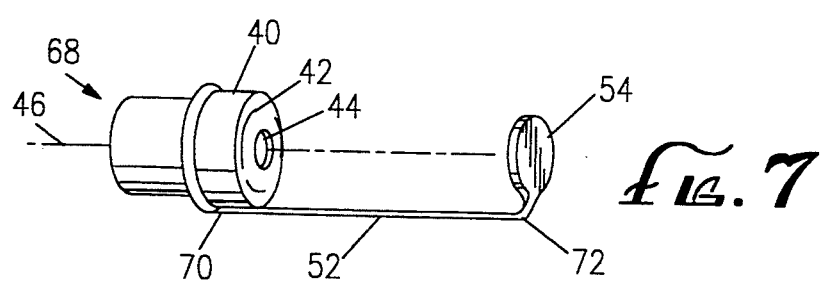

APPARATUS AND METHOD FOR DETERMINING A PATIENT'S DOMINANT EYE

BACKGROUND

This invention is directed to an apparatus and a method for determining an individual's preferred eye in a binocular situation where the preferred eye controls the visual pattern.

Research has shown that in a binocular situation where both eyes provide visual input, one eye controls the visual pattern. The controlling eye is the lead or preferred eye. Each individual also has a preferred ear, and a preferred hand. Alignment of these faculties has a significant effect on the ability of an individual to perform certain key activities such as reading. For example, good readers tend to be in perfect alignment or "sidedhess." They are either left-eye-left-handed or right-eye-right-handed. Conversely, poor readers tend to have a mixed "sidedness" (left-eye-right-handed or vice versa).

Research has also shown that "sidedness" is a prerequisite to learning visually, auditorially, and kinesthetically. A significant number of individuals with mixed eye-ear-hand preference experience learning difficulties, particularly in the area of reading. The majority of these individuals were changed to mixed "sidedness" because of cultural or ethnic superstitions. For example, Asian and Hispanic immigrants are most vulnerable to mixed "sidedness".

Accordingly, diagnostic techniques to detect learning problems must include "sidedness" as a factor. Further, parents and teachers must be reeducated regarding the importance of "sidedness" as it relates to the learning process. Thus, determining "sidedness" at an early age (5 to 7 years) will significantly impact the success of the learner. It is more advantageous to begin the learning process correctly than to remediate and attempt to reverse bad habits and practices.

However, determining eye preference has generally been limited to cases where an individual suffers from a visual atrophy unconnected to "sidedness." The case arises when one eye is defective and one eye is normal. Because the individual has to rely on the normal eye for proper vision, the normal eye is designated as the preferred eye. This designation, however, should not be mistaken with the case where both eyes are normal but the individual has simply developed a preference for one eye to control the visual pattern, namely the preferred eye.

The testing devices and procedures utilized in detecting visual atrophy in one eye are geared towards detection of a defective eye. They are not capable of efficient and accurate determination of eye preference in normal eyes.

The most relevant case in which a device designed for determining eye defects may possibly be used for determining eye preference in normal eyes, is in a case where the examining device is designed to detect blind spots in one eye. There, color slides are placed in front of each eye and the concept of fusion is used to determine the defective eye. If there is a lack of fusion, the preferred (i.e. normal) eye will be manifest through color response of the individual. In other words, if one eye is normal, the fused color will be tinted by the color entering the normal eye.

However, this approach is inefficient and inaccurate in determining eye preference when both eyes are normal. First, the approach relies on fusion which, in the case of normal eyes, will not reveal any detectable difference between the eyes. Second, the procedure is time consuming since several slides must be viewed in order to obtain reliable test results. Third, due to the complexity of the test, it must be administered by a trained professional at substantial cost.

Recently, the "differentiation" test has been utilized by optometrists to determine eye preference in normal eyes. However, this procedure requires the services of an optometrist at a substantial cost. Moreover, it takes approximately 50 minutes to administer the test.

Accordingly, there is a need for an eye examining device to determine eye preference in normal eyes in a short period of time. There is also a need for such a device to produce very accurate results in that short period of time. There is also a need for such a device to not require the services of an eye professional in its operation. There is also a need for such a device to be simple to use. There is also a need for such a device to be inexpensive.

SUMMARY OF THE INVENTION

The invention satisfies these needs.

The invention provides an examining device comprising: (a) a viewing port, (b) a face support disposed spaced apart from, and behind, the viewing port, the face support being adapted to receive and retain the face of a user so as to hold the eyes of the user in fixed relationship to the viewing port, the face support having one or more eye ports so that (i) the user can see through the viewing port with the user's right eye along a single right eye line of sight and (ii) the user can see through the viewing port with the user's left eye along a single left eye line of sight, (c) a first blocking device for alternatively blocking and unblocking the right eye line of sight, and (d) a second blocking device for alternatively blocking and unblocking the left eye line of sight.

In a preferred embodiment of the invention, the examining device further comprises a cap attached to the viewing port, the cap having sidewalls and a head plate, the head plate having an opening to allow for the passage of light through the viewing port. The head plate opening is disposed proximate to, but forward of, the furthermost point where the left and the right eye lines of sight can meet in front of the viewing port when neither line of sight through the viewing port is blocked.

In another embodiment of the invention, the examining device further comprises a support for disposing a target in front of the viewing port, wherein the target is disposed proximate to, but forward of, the furthermost point where the left and the right eye lines of sight can meet in front of the viewing port when neither line of sight through the viewing port is blocked.

In a preferred embodiment of the examining device discussed in the immediately preceding paragraph, the support comprises a beam with a first end and a second end, the first end being attached to the periphery of the viewing port with the beam extending forwardly in front of the viewing port, and the target being attached to the second end of the beam.

In another embodiment of the invention, the first and second blocking devices are one and the same comprising a slide disposed in front of the face support, but behind the viewing port, the slide being transverse to the lines of sight and having a central opening which is dimensioned such that (a) neither line of sight is blocked when the slide is centered relative to the viewing port, (b) the right line of sight is blocked when the slide is located to the extreme left of its center position, and (c) the left eye line of sight is blocked when the slide is located to the extreme right of its center position.

The invention provides an extremely simple yet effective way for determining a preferred eye in an individual. No complicated apparatus or expensive equipment is provided. The invention merely employs a few components and utilizes ambient light. It is an extremely cost effective and time efficient instrument which allows the examiner to detect eye preference in less than 30 seconds with nearly 100% accuracy.

DESCRIPTION OF THE DRAWINGS

These and other features, aspects and advantages of the present invention will become understood with reference to the following description, appended claims and accompanying drawings where:

FIG. 4 is a view of the examining device of FIG. 2 along line 4—4;

FIG. 4a is another view of the examining device of FIG. 2 along line 4—4;

FIG. 4b is yet another view of the examining device of FIG. 2 along line 4—4;

FIG. 5 is a perspective view of an embodiment of a detachable cap for the viewing port of the examining device of FIG. 2;

FIG. 6 is a perspective view of another embodiment of a detachable cap for the viewing port of the examining device of FIG. 2;

FIG. 7 is a perspective view of yet another embodiment of a detachable cap for the viewing port of the examining device of FIG. 2.

DESCRIPTION OF THE INVENTION

The following discussion describes in detail several embodiments of the invention. This discussion should not be construed, however, as limiting the invention to those particular embodiments. Practitioners skilled in the art will recognize numerous other embodiments as well. For definition of the complete scope of the invention, the reader is directed to the appended claims.

Figure 2:
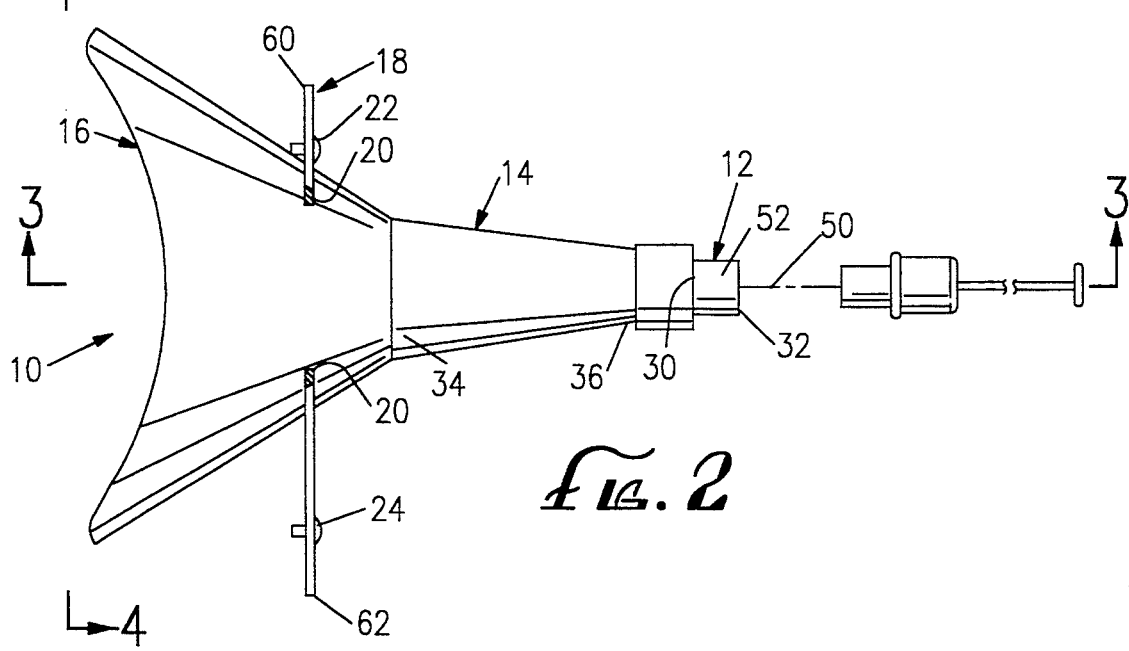
FIG. 2 is a top view of an eye examining device embodying the features of the invention.

Referring to the drawings, an eye examining device 10 embodying features of the invention is shown in FIG. 2. The examining device 10 comprises (a) a viewing port 12, (b) a face support 16 adapted to receive and retain the face of a user 80 so as to hold the eyes of the user 80 in fixed relationship to the viewing port 12, (c) a first blocking device for alternatively blocking and unblocking the right eye line of sight 84 of the user 80, and (d) a second blocking device for alternatively blocking and unblocking the left eye line of sight 82 of the user 80.

The viewing port 12 has a front 32, a back 30, and a longitudinal axis 50. The viewing port 12 can comprise a cylindrical sidewall 52 forming an opening 28 extending from the front 32 of the viewing port 12 to the back 30 of the viewing port 12. The opening 28 allows the passage of light through the viewing port opening 28. The sidewall 52 can be of any suitable shape for forming a viewing port with an opening for the passage of light therethrough. In a preferred embodiment of the invention the area of the viewing port opening 28 is about 2 square centimeters. In a typical embodiment of the invention, the sidewall 52 is made out of an opaque and rigid material such as plastic. Other materials such as wood, aluminum, etc. may also be used.

In a typical embodiment of the invention the examining device 10 further comprises a sidewall 14. Referring to the embodiment shown in FIG. 3, the sidewall 14 is conical in shape with a narrow end 36, a wide end 34, and a longitudinal axis 56. The narrow end 36 of the sidewall 14 is attached to the back 30 of the viewing port 12 such that the longitudinal axes of the viewing port 12 and the sidewall 14 coincide. In a typical embodiment of the invention, the narrow end 36 of the side wall 14 is of the same diameter as that of the viewing port opening 28. The sidewall 14 can be made of any opaque and rigid material such as plastic, aluminum, etc.

The face support 16 is adapted to receive and retain the user's face. The face support 16 is attached to the wide end 34 of the sidewall 14. In a typical embodiment of the invention, such as the embodiment shown in FIG. 2, the face support 16 can be an extension of the sidewall 14.

Figure 1:
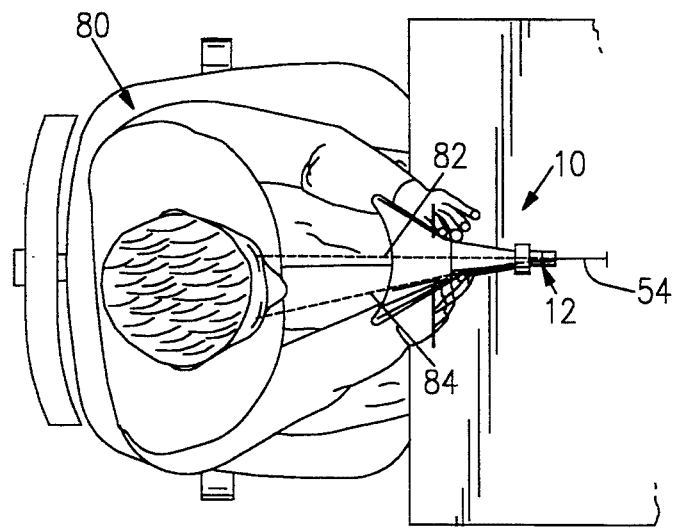
FIG. 1 is a top view of an eye examining device embodying the features of the invention as held by a user.

As so assembled, the examining device 10 enables the user 80 to see through the viewing port 12 along the user's left and right eye lines of sight, 82 and 84 respectively, and through the viewing port 12 as shown in FIG. 1.

Figure 8:
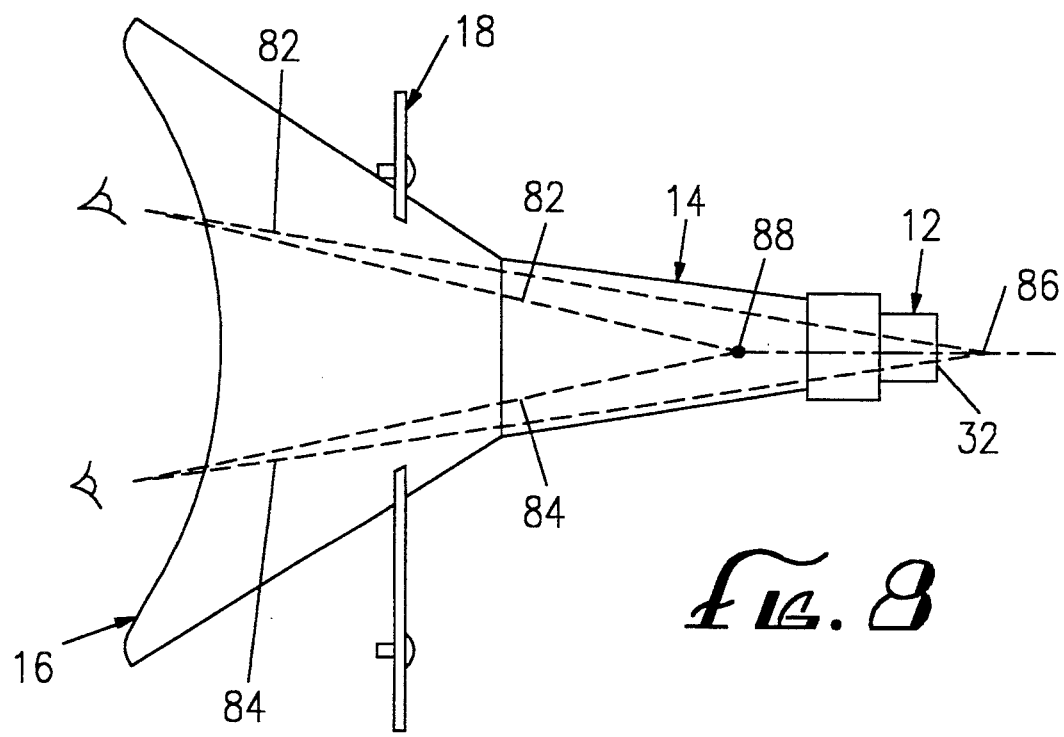
FIG. 8 is a top view of an eye examining device embodying the features of the invention.

In a typical embodiment of the invention shown in FIG. 8, the viewing port 12, the sidewall 14, and the face support 16 are dimensioned such that the furthermost point 86 where the left eye line of sight 82 and the right eye line of sight 84 through the viewing port 12 can meet is proximate to, but forward of, the front 32 of the viewing port 12. The left and right eye lines of sight, 82 and 84 respectively, can also meet at a point such as point 88 wherein point 88 is behind the furthermost point 86 described above.

In the embodiments shown in the drawings the first and second blocking devices are provided by the slide 18. The slide 18 has a left end 60 and a right end 62. The slide 18 is disposed in guide slots 20 defined in the sidewall 14 such that the plane of the slide 18 is transverse to the right eye line of sight 84, to the left eye line of sight 82, and to the longitudinal axis 56 of the side wall. The slide 18 is disposed in front of the face support 16, but behind the viewing port 12. The guide slots 20 are dimensioned such that the slide 18 can only be moved in a plane transverse to the lines of sight and to the longitudinal axis 54 of the side wall 14.

The slide 18 further comprises a left stop bar 22 disposed on the slide proximate to the left end 60 of the slide 18, and a right stop bar 24 disposed on the slide 18 proximate to the right end 62 of the slide 18. The left stop bar 22 limits the sliding motion of the slide 18 through the guide slots 20 to an extreme right as shown in FIG. 4a, and the right stop bar 24 limits the sliding motion of the slide 18 through the guide slots 20 to an extreme left as shown in FIG. 4b.

As shown in FIGS. 4, 4a, and 4b, the slide 18 further comprises an opening 26 through the plane of the slide 18. The opening 26 is dimensioned such that (i) neither line of sight through the viewing port 12 is blocked when the slide 18 is in its center position, shown in FIG. 4, wherein the center of the opening 26 coincides with the longitudinal axis 50 of the viewing port 12, (ii) the right eye line of sight 84 through the viewing port 12 is blocked when the slide 18 is located to the extreme left of its center position as limited by the right stop bar 24, and (iii) the left eye line of sight 82 through the viewing port 12 is blocked when the slide 18 is located to the extreme right of its center position as limited by the left stop bar 22.

In a preferred embodiment of the invention, the opening 26 of the slide is disposed in the center of the slide 18 relative to the right end 62 and the left 60 end of the slide 18. The opening 26 can be substantially rectangular in shape. The slide 18 can be made of any opaque and rigid material such as aluminum, copper, wood, etc.

In a typical embodiment of the invention, the examining device 10 further comprises one or more detachable caps for the viewing port 12. Referring to FIG. 5, a cap 64 has a sidewall 40, a head plate 42, and a longitudinal axis 46. The head plate 42 has an opening 44 in its center to allow for the passage of light through the viewing port 12. The cap 64 is attached to the front 32 of the viewing port 12 such that the longitudinal axes of the cap 64 and the viewing port 12 coincide. As so attached, the cap opening 44 is disposed proximate to, but forward of, the furthermost point where the left and the right eye lines of sight can meet in front of the viewing port 12 when neither line of sight through the viewing port 12 is blocked.

In a preferred embodiment of the invention the cap 64 is cylindrical in shape and made out of an opaque and rigid material such as copper. The opening 44 in the head plate 42 can be circular with an area smaller than that of the viewing port opening 28.

FIG. 6 shows another cap 66 as described in the two immediately preceding paragraphs where the size of the opening 44 in the head plate 42 is less than about 0.01 square centimeters.

In another embodiment of the invention the examining device 10 further comprises a support for disposing a target in front of the viewing port 12, wherein the target is disposed proximate to, but forward of, the furthest most point where the left and the right eye lines of sight can meet in front of the viewing port 12 when neither line of sight is blocked. The target can be disposed at a distance of about 16 inches away from the face support.

Figure 3:
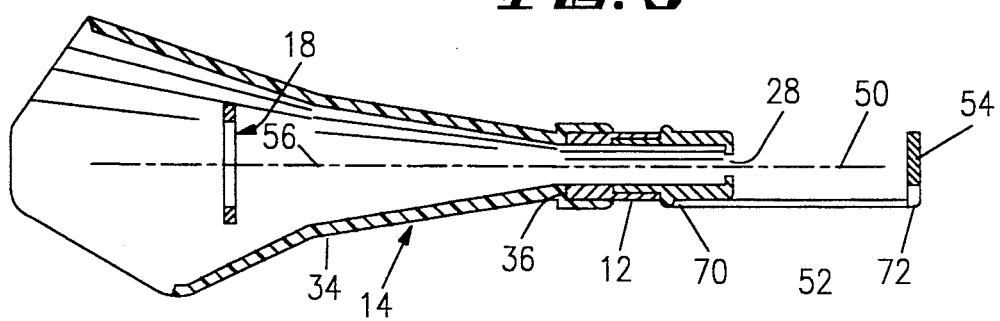
FIG. 3 is a cross section of the examining device of FIG. 2 along line 3—3.

In the embodiment shown in FIG. 3, the support comprises a beam 52 with a first end 70 and a second end 72, the first end 70 being attached to an external surface of the viewing port 12 with the beam 52 extending forwardly in front of the viewing port 12, and the target 54 being attached to the second end 72 of the beam 52.

In a most preferred embodiment of the invention shown in FIG. 7, a cap 68, identical to the cap 64 of FIG. 5 described above, is utilized to dispose the target 54 in front of the viewing port 12 wherein the first end 70 of the support beam 52 is attached to an external surface of the side wall 40 of the cap 68.

The support beam 52 and the target 54 can be made from any rigid material such as copper or aluminum. The target 54 can be circular in shape with a diameter less than that of the viewing port opening 28.

In operation, left or right eye preference is tested by (a) placing the face of the person being examined against the face support 16 of the examining device 10 described above and shown in FIG. 2, (b) adjusting the slide 18 such that neither line of sight is blocked, (c) orienting the examinee such that an object which is beyond the furthermost point where the left eye line of sight 82 and the right eye line of sight 84 can meet in front of the viewing port 12 is visible through the viewing port 12, and asking the examinee to pivot the examining device 10, as held against the examinee's face, in a horizontal plane such that the examinee can focus on the object visible through the viewing port 12, (d) blocking one of the two lines of sight without blocking the other by sliding the slide 18 to one of its extreme limits, and asking the examinee if the object is still visible, and (e) blocking the other line of sight without blocking the first by sliding the slide 18 to its other extreme limit, and asking the examinee if the object is still visible.

Left or right eye preference is further tested by (a) placing the face of the person being examined against the face support 16 of the examining device 10 described above wherein the examining device 10 further comprises of the detachable cap 64 of FIG. 5, (b) adjusting the slide 18 such that neither line of sight is blocked, (c) orienting the examinee such that an object visible through the viewing port 12 is at a distance of 20 feet or more from the examinee's eyes and asking the examinee to pivot the examining device 10, as held against the examinee's face, in a horizontal plane such that the examinee can focus on the object visible through the viewing port 12, (d) blocking one of the two lines of sight without blocking the other by sliding the slide 18 to one of its extreme limits, and asking the examinee if the object is still visible, and (e) blocking the other line of sight without blocking the first by sliding the slide 18 to its other extreme limit, and asking the examinee if the object is still visible.

Left or right eye preference is further tested by (a) placing the face of the person being examined against the face support 16 of the examining device 10 described above wherein the examining device 10 further comprises of the detachable cap 66 of FIG. 6, (b) adjusting the slide 18 such that neither line of sight is blocked, (c) orienting the examinee such that an object visible through the viewing port 12 is at a distance of 1 to 2 inches away from the cap opening 44 and asking the examinee to pivot the examining device 10, as held against the examinee's face, in a horizontal plane such that the examinee can focus on the object visible through the viewing port 12, (d) blocking one of the two lines of sight without blocking the other by sliding the slide 18 to one of its extreme limits, and asking the examinee if the object is still visible, and (e) blocking the other line of sight without blocking the first by sliding the slide 18 to its other extreme limit, and asking the examinee if the object is still visible.

Left or right eye preference is further tested by (a) placing the face of the person being examined proximate to the face support 16 of the examining device 10 described above wherein the examining device 10 further comprises of the detachable cap 68 of FIG. 7, (b) adjusting the slide such that neither line of sight is blocked, (c) orienting the examinee such that the target 54 is a distance of about 16 inches from the examinee's eyes, as shown in FIG. 1, and asking the examinee to pivot the examining device 10, as held against the examinee's face, in a horizontal plane such that the examinee can focus on the target 54 visible through the viewing port 12, (d) blocking one of the two lines of sight without blocking the other by sliding the slide 18 to one of its extreme limits, and asking the examinee if the target 54 is still visible, and (e) blocking the other line of sight without blocking the first by sliding the slide 18 to its other extreme limit, and asking the examinee if the target 54 is still visible.

What is claimed is:

1. An examining device comprising:
   (a) a viewing port comprising a perimeter structure with an aperture;
   (b) a face support disposed spaced apart from the viewing port, the face support being adapted to receive and retain the face of the user so as to hold the eyes of the user in fixed relationship to the viewing port, the face support having one or more eye ports so that (i) the user can see through the viewing port with the user's right eye along a single right eye line of sight, and (ii) the user can see through the viewing port with the user's left eye along a single left eye line of sight;
   (c) a first blocking device for alternatively blocking and unblocking the right eye line of sight;
   (d) a second blocking device for alternatively blocking and unblocking the left eye line of sight; and
   (e) a cap attached to the viewing port in such a way that the viewing port is disposed between the cap and the face support, the cap having sidewalls and a head plate disposed opposite the viewing port, the head plate having an opening to allow for the passage of light through the viewing port to the face support;
   wherein the head plate opening is disposed so that the furthermost point from the face support where the left and the right eye lines of sight can meet when neither line of sight through the viewing port is blocked is located between the viewing port and the head plate opening.

2. The device of claim 1 wherein the area of the head plate opening is less than about 0.01 square centimeters.

3. The device of claim 1 further comprising a target disposed so that the furthermost point from the face support where the left and the right eyes of sight can meet when neither line of sight through the viewing port is blocked is located between the viewing point and the target.

4. The device of claim 3 wherein the target is disposed at a distance of approximately 16 inches away from the face support.

5. An examining device comprising:
   (a) a viewing port comprising a perimeter structure with an aperture;
   (b) a face support disposed spaced apart from the viewing port, the face support being adapted to receive and retain the face of the user so as to hold the eyes of the user in fixed relationship to the viewing port, the face support having one or more eye ports so that (i) the user can see through the viewing port with the user's right eye along a single right eye line of sight, and (ii) the user can see through the viewing port with the user's left eye along a single left eye line of sight;
   (c) a first blocking device for alternatively blocking and unblocking the right eye line of sight; and
   (d) a second blocking device for alternatively blocking and unblocking the left eye line of sight;
   wherein the first and second blocking devices are the same and comprise a slide disposed between the face support and the viewing port, the slide being transverse to the lines of sight and having a central opening which is dimensioned such that (a) neither line of sight is blocked when the slide is centered relative to the viewing port, (b) the right eye line of sight is blocked when the slide is located to the extreme left of its center position, and (c) the left eye line of sight is blocked when the slide is located to the extreme right of its center position.

6. An examining device comprising:
   (a) a viewing port;
   (b) a face support disposed spaced apart from the viewing port, the face support being adapted to receive and retain the face of the user so as to hold the eyes of the user in fixed relationship to the viewing port, the face support having one or more eye ports so that (i) the user can see through the viewing port with the user's right eye along a single right eye line of sight and (ii) the user can see through the viewing port with the user's left eye along a single left eye line of sight;
   (c) conical sidewalls with a narrow end and a wide end, the viewing port being attached to the narrow end, and the face support being attached to the wide end, wherein the longitudinal axes of the viewing port and the face support coincide with the longitudinal axis of the sidewalls; and
   (d) a blocking device for (i) alternatively blocking and unblocking the right eye line of sight; and (ii) for alternatively blocking and unblocking the left eye line of sight, the blocking device comprising a slide attached to the sidewalls, the slide being transverse to the lines of sight and to the longitudinal axis of the sidewalls, the slide having a central opening which is dimensioned such that (i) neither line of sight is blocked when the slide is centered relative to the viewing port, (ii) the right eye line of sight is blocked when the slide is located to the extreme left of its center position, and (iii) the left eye line of sight is blocked when the slide is located to the extreme right of its center position.

7. The device of claim 6 further comprising a target disposed so that the furthermost point from the face support where the left and the right eyes of sight can meet when neither line of sight through the viewing port is blocked is located between the viewing point and the target.

8. The device of claim 7 wherein the target is disposed at a distance of approximately 16 inches away from the face support.

9. A kit for eye examination comprising:
   (a) an examining device comprising:
      (i) a viewing port;
      (ii) a face support disposed spaced apart from the viewing port, the face support being adapted to receive and retain the face of the user so as to hold the eyes of the user in fixed relationship to the viewing port, the face support having one or more eye ports so that (1) the user can see through the viewing port with the user's right eye along a single right eye line of sight and (2) the user can see through the viewing port with the user's left eye along a single left eye line of sight;
      (iii) conical sidewalls with a narrow end and a wide end, the viewing port being attached to the narrow end, and the face support being attached to the wide end, wherein the longitudinal axes of the viewing port and the face support coincide with the longitudinal axis of the sidewalls;

(iv) a blocking device for (1) alternatively blocking and unblocking the right eye line of sight; and (2) for alternatively blocking and unblocking the left eye line of sight, the blocking device comprising a slide attached to the sidewalls, the slide being transverse to the lines of sight and to the longitudinal axis of the sidewalls, the slide having a central opening which is dimensioned such that (1) neither line of sight is blocked when the slide is centered relative to the viewing port, (2) the right eye line of sight is blocked when the slide is located to the extreme left of its center position, and (3) the left eye line of sight is blocked when the slide is located to the extreme right of its center position; and (b) one or more detachable caps for the viewing port, each cap being attachable to the viewing port in such a way that the viewing port is disposed between the cap and the face support, each cap having sidewalls and a head plate disposed opposite the viewing port, the head plate having an opening to allow for the passage of light through the viewing port, wherein the head plate opening is disposed so that the furthermost point from the face support where the left eye and the right eye lines of sight can meet when neither line of sight through the viewing port is blocked is located between the viewing port and the head plate opening.

10. The kit of claim 9 wherein the area of the head plate opening in one of the caps is less than about 0.01 square centimeters.

11. The device of claim 9 wherein at least one of the caps has a target disposed so that, when the cap with the target is attached to the viewing port, the target is disposed at a distance of approximately 16 inches away from the face support.

12. A method of testing left or right eye preference comprising the steps of:

(a) placing the face of the person being examined against the face support of an examining device comprising:

(i) a viewing port;

(ii) a face support disposed spaced apart from the viewing port, the face support being adapted to receive and retain the face of the examinee so as to hold the eyes of the examinee in fixed relationship to the viewing port, the face support having one or more eye ports so that (1) the examinee can see through the viewing port with the examinee's right eye along a single right eye line of sight and (2) the examinee can see through the viewing port with the examinee's left eye along a single left eye line of sight;

(iii) a first blocking device for alternatively blocking and unblocking the right eye line of sight;

(iv) a second blocking device for alternatively blocking and unblocking the left eye line of sight;

(b) adjusting the blocking devices such that neither line of sight is blocked;

(c) orienting the examinee such that an object which is beyond the furthermost point where the left eye line of sight and the right eye line of sight can meet in front of the viewing port, is visible through the viewing port and asking the examinee to pivot the device, as held against the examinee's face, in a horizontal plane such that the examinee can focus on the object visible through the viewing port;

(d) blocking one of the two lines of sight without blocking the other, and asking the examinee if the object is still visible; and (e) blocking the other line of sight without blocking the first, and asking the examinee if the object is still visible.

13. The method of claim 12 wherein the examining device further comprises a cap attached to the viewing port in such a way that the viewing port is disposed between the cap and the face support, the cap having sidewalls and a head plate disposed opposite the viewing port, the head plate having an opening to allow for the passage of light through the viewing port to the face support, wherein the head plate opening is disposed so that the furthermost point where the left eye line of sight and the right eye line of sight can meet when neither line of sight through the viewing port is blocked is located between the viewing port and the head plate opening.

14. The method of claim 13 wherein the area of the head plate opening in the cap is less than about 0.01 square centimeters.

15. The method of claim 12 wherein the examining device further comprising a target disposed so that the furthermost point from the face support where the left and the right eye lines of sight can meet when neither line of sight through the viewing port is blocked is located between the viewing port and the target;

wherein step (c) is as follows:

(c) adjusting the distance from the examinee's face at the face support to the target so that such distance is approximately 16 inches away from the examinee's eyes and asking the examinee to pivot the device, as held in front of the examinee's face, in a horizontal plane such that the examinee can focus on the target visible through the viewing port.

* * * * *